United States Patent [19]

Wolvek et al.

[11] 4,111,209

[45] Sep. 5, 1978

[54] TOPICAL HYPOTHERMIA APPARATUS AND METHOD FOR TREATING THE HUMAN BODY AND THE LIKE

[75] Inventors: Sidney Wolvek, Brooklyn, N.Y.; Bruce L. Hanson, Wayne, N.J.; David Bregman, New York, N.Y.

[73] Assignee: Datascope Corporation, Paramus, N.Y.

[21] Appl. No.: 788,228

[22] Filed: Apr. 18, 1977

[51] Int. Cl.² ............................................. A61F 7/00
[52] U.S. Cl. ................................... 128/400; 128/401
[58] Field of Search ............ 128/400, 401, 399, 344, 128/303.11, 303.12

[56] References Cited

U.S. PATENT DOCUMENTS

| | | | |
|---|---|---|---|
| 2,190,383 | 2/1940 | Newman | 128/401 |
| 2,319,542 | 5/1943 | Hall | 128/400 |
| 2,429,238 | 10/1947 | Restarski et al. | 128/400 |
| 3,439,681 | 4/1969 | Riley | 128/401 |
| 3,738,372 | 6/1973 | Shioshvili | 128/400 |

FOREIGN PATENT DOCUMENTS

| | | | |
|---|---|---|---|
| 189,975 | 10/1939 | Switzerland | 128/401 |
| 281,489 | 11/1967 | U.S.S.R. | 128/401 |

*Primary Examiner*—Lawrence W. Trapp
*Attorney, Agent, or Firm*—Martin G. Raskin

[57] ABSTRACT

Apparatus and method for providing hypothermia or effecting hemostasis to prevent hemorrhaging in organs or regions of the human body and the like. In one application described herein, the apparatus provides hypothermia to the heart during, for example, cardio-pulmonary bypass. The apparatus comprises a unitary preferably disposable coolant fluid circuit, including a length of flexible tubing having a heat exchange portion and a flexible, inflatable bag through which a sterile coolant fluid passes. The inflatable bag is connected to the flexible tubing by a double lumen. The tubing is provided with appropriate fittings proximate to its juncture with the double lumen to allow introduction of coolant fluid. The heat exchanger portion of the coolant fluid circuit is located within a preferably disposable container which contains refrigeration means for reducing the temperature of the coolant fluid. A pump is provided which operates externally to the coolant fluid circuit in order to cause the coolant fluid to circulate therethrough.

Just prior to locating the bag into proximity with the organ to be treated, the fluid circuit is filled with coolant fluid by parting the tubing at the fitting (which may comprise a three-way petcock) and introducing the coolant fluid with the bag maintained in a deflated condition. The bag is then appropriately located proximate to or within the organ, the tubing joined and the bag distended by introducing additional coolant fluid through the fitting using a syringe of the like.

5 Claims, 12 Drawing Figures

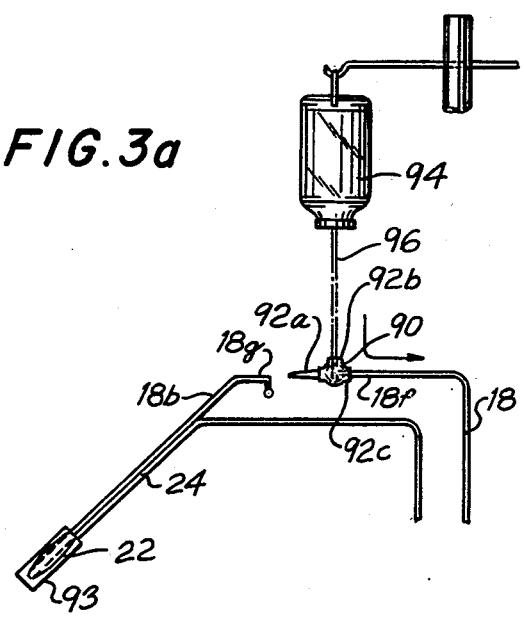
FIG.3a
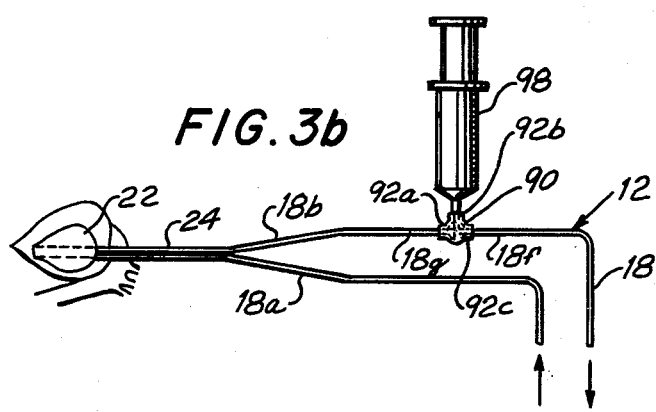
FIG.3b
FIG.5a
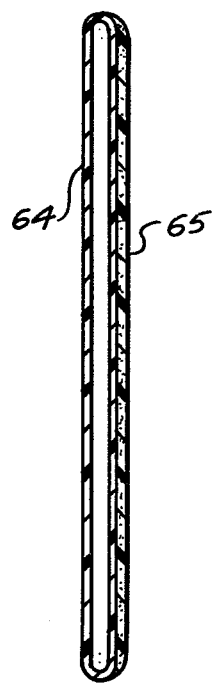
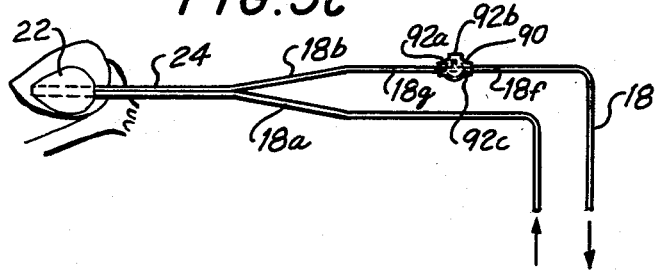
FIG.3c
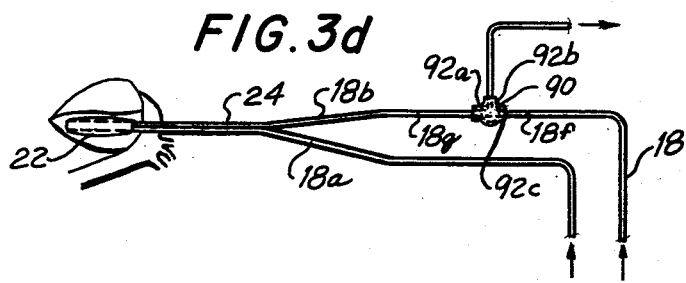
FIG.3d

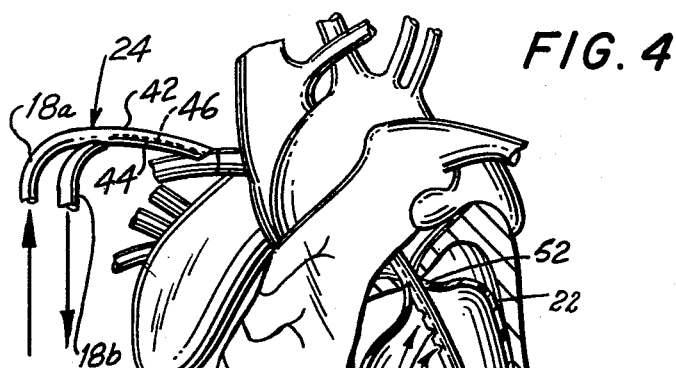
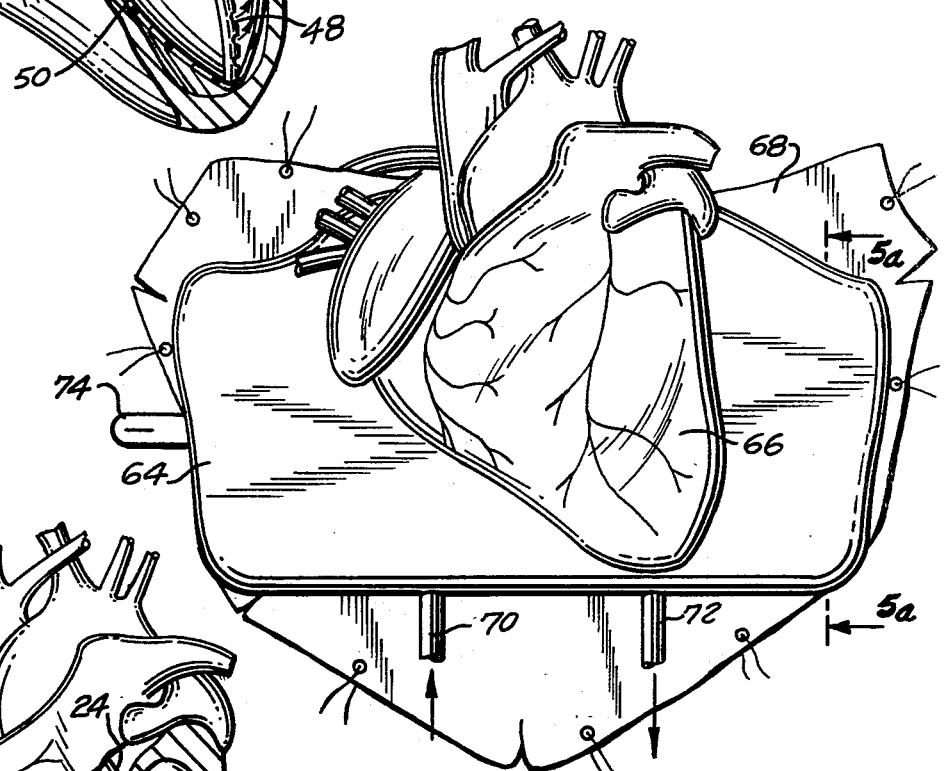
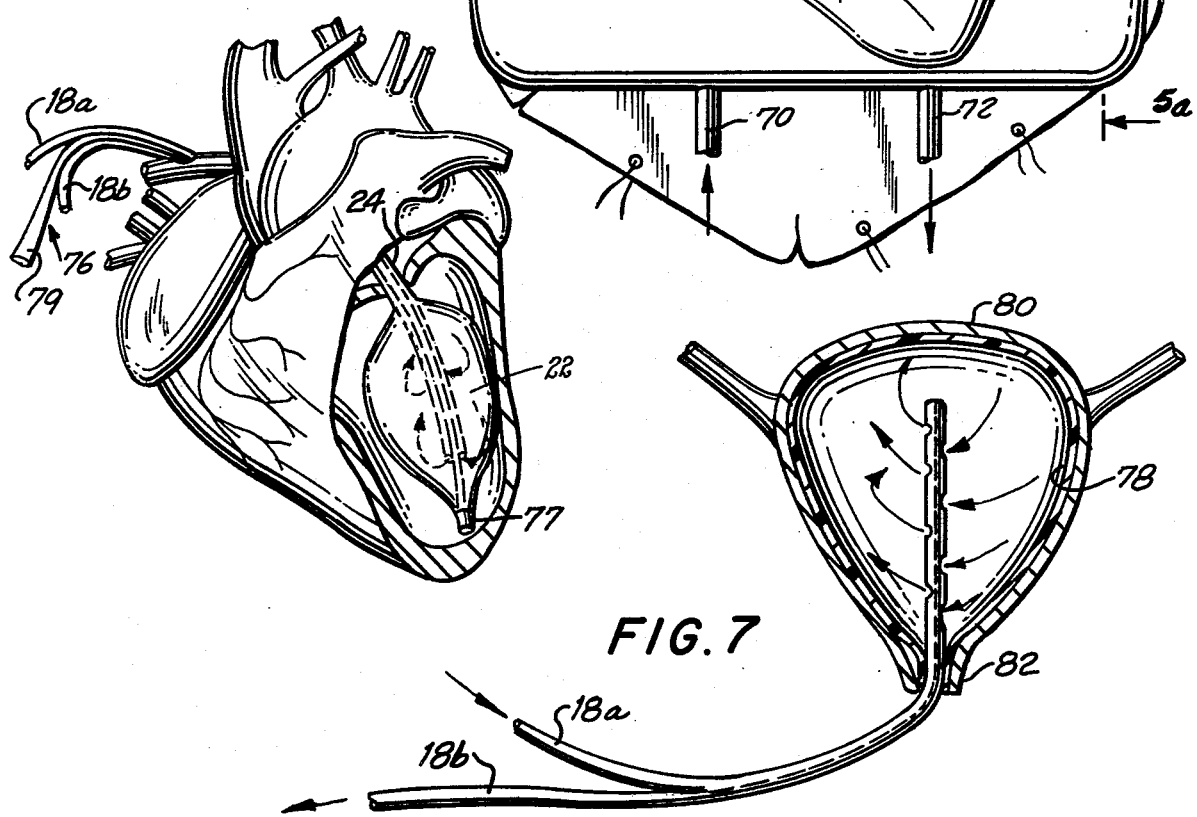

TOPICAL HYPOTHERMIA APPARATUS AND METHOD FOR TREATING THE HUMAN BODY AND THE LIKE

BACKGROUND OF THE INVENTION

This invention relates to methods and apparatus for providing hypothermia or effecting hemostasis to prevent hemorrhaging in organs or regions within the human body or the like.

Topical hypothermia of organs or regions within the body has been proposed in the past. Examples of such proposed systems are disclosed in U.S. Pat. Nos. 3,460,538 granted on Aug. 12, 1969 to Armstrong, 3,738,372 granted June 12, 1973 to Shioshvili and in "A Simple Cooling Circuit for Topical Cardiac Hypothermia," Thorax, Vol. 31, pp. 565–571 (1976).

Such previously proposed systems are each deficient in one or more respects. Firstly, in those systems which utilize inflatable bags, none provides means by which the bag may be distended subsequent to its location or insertion proximate the organ to be treated so that its walls are in optimal cooling contact with the walls of the organ. Secondly, in most systems the continued sterility of the coolant fluid during operation cannot be assured. Thirdly, all of the previously proposed systems include apparatus which are bulky and difficult to assemble which make them practically unsuitable for use in an operating room as well as expensive in manufacture.

Further, although it is standard procedure to lower the blood temperature during cardio-pulmonary support (such as during open heart surgery) by means of a heat exchanger incorporated into the pump-oxygenator circuitry, this systemic hypothermia, while decreasing cellular metabolism and preventing cellular damage from anoxia, will not provide hypothermic protection to the myocardium of the heart when the aorta is occluded, thereby depriving the heart and the coronary arteries of cardiopulmonary support. Generally, two methods of achieving topical cardiac hypothermia have been used. The opened pericardium has been filled with a frozen saline slush, or, alternatively, the pericardial "basin" has been irrigated along with the heart surface with cooled Lactated Ringer's solution via a drip bottle and wall suction (See Thorax article referred to hereinabove). However, neither of these methods provide direct cooling to the endocardium or inner wall of the heart. Both methods rely on introducing free fluid or slush within the open pericardium and, therefore, the patient must be appropriately positioned to maintain the cold fluid within the pericardial basin without spillage. This requirement and the usual difficulties inherent in the use of a fluid in an unconfined state render both of these techniques less desirable.

Although some surgeons have filled an open ventricle with saline slush in an attempt to cool the myocardium, this has been found to be a rather clumsy procedure involving, among other problems, the necessity for the surgeon to perform delicate surgical techniques with his fingers in an ice cold solution. Additionally, some surgeons have attempted to apply cardiac hypothermia by introducing cannulae into the openings of the coronary arteries which lie in the aortic root immediately adjacent to the heart. Cold perfusate is then pumped into the coronary arteries and retrieved by suction from the right atrium and/or coronary sinus. However, since much of the cardiac surgery is performed on these coronary arteries and in the aortic root this procedure has found only limited application and, consequently, is of limited value.

SUMMARY OF THE INVENTION

Accordingly, one object of the present invention is to provide a new and improved apparatus and method for the application of hypothermia in a safe and efficient manner.

Another object of the present invention is to provide an apparatus for the application of topical hypothermia including a preferably disposable, coolant circuit including a heat exchange section portion and a preferably disposable coolant chamber.

Still another object of the present invention is to provide apparatus for the application of topical hypothermia which is relatively economical in use and manufacture.

A further object of the present invention is to provide a method and apparatus for cardiac hypothermia during open heart surgery.

A still further object of the present invention is to provide an apparatus for cooling the inner surface of the heart.

Yet another object of the present invention is to provide an apparatus and method for arresting hemorrhaging from body cavities by a combination of cooling and internal pressure.

Yet still another object of the present invention is to provide an apparatus for the application of topical hypothermia or hemostasis including an inflatable bag to be located in proximity with the organ or area to be treated and which bag may be filled with coolant fluid in a manner by which its walls will be in optimum heat exchange relationship with the walls of the organ to be treated.

Briefly, these and other objects are attained by providing apparatus comprising preferably disposable components and a permanent pump component. The disposable components include a fluid coolant circuit including a length of flexible tubing having a heat exchange portion fluidly connected to a double lumen and a flexible, inflatable bag.

The tubing is provided with appropriate fittings (including, for example, a three-way petcock) proximate to its juncture with the double lumen to allow introduction of coolant fluid. A preferably disposable container is provided within which the heat exchange portion of the tubing is located, the container being filled with an ice-water solution during operation of the invention.

The permanent components of the apparatus include a pump of the roller type which is operatively associated with the exterior of the walls of the flexible tubing and which, therefore, cannot threaten the sterility of the coolant fluid circulating within the coolant circuit.

Just prior to locating the bag into proximity with the organ to be treated, the fluid circuit is filled with coolant fluid by parting the tubing at the fitting and introducing the coolant fluid with the bag maintained in a deflated condition. The bag is then appropriately located proximate to or within the organ, the tubing joined, and the bag distended by introducing additional coolant fluid through the fitting using a syringe or the like. The amount of additional fluid introduced is predetermined depending upon the surface area of the walls and volume of the interior of the organ being treated.

In another embodiment of the apparatus, a third passage is provided either in the form of a triple lumen in lieu of the double lumen or via a catheter, one end of the third passage extending entirely through the inflatable bag with the other end communicating with the outside environment. The third passage is used for venting air from the cavity which is to be hypothermically treated.

The flexible, inflatable bag may be appropriately formed so as to be introduceable into one of the chambers of the heart, for example, the left ventricle, through a pulmonary vein. The bag may also be provided in the form of a substantially thin bladder (which may have a thermal insulation barrier provided on its outer wall) for location behind the organ to be hypothermically treated and then folded therearound for applying topical hypothermia to substantially the entire outer wall of the organ.

Of course, the bag may be provided in any configuration and and the catheter or tubing section may be marked with appropriate indicia to identify the direction and orientation in which the bag in its deflated condition is to be inserted. The bag and bladder may be used separately as substitutes for each other as described hereinbelow, or at the same time.

DESCRIPTION OF THE DRAWINGS

A more complete appreciation of the invention and many of the attendant advantages thereof will be readily appreciated as the same becomes better understood by reference to the following detailed description when considered in connection with the accompanying drawings wherein:

FIGS. 3 (a–d) are schematic illustrations of the sequence of filling the coolant circuit of the present invention with coolant fluid;

FIG. 4 is a perspective view, partially broken away, of an inflatable bag located within the left ventricle of the heart according to the present invention;

FIG. 5 is a perspective view showing another embodiment of the flexible bag for use in hypothermically treating the myocardium or outer surface of the heart;

FIG. 5a is a section view taken along line 5a—5a of FIG. 5;

FIG. 6 is a view similar to FIG. 4 wherein a third passage is provided through the flexible bag;

FIG. 7 is a sectional schematic view illustrating the use of a modified form of the invention for arresting homorrhaging in a body cavity or organ.

DESCRIPTION OF THE PREFERRED EMBODIMENTS

Figure 1:
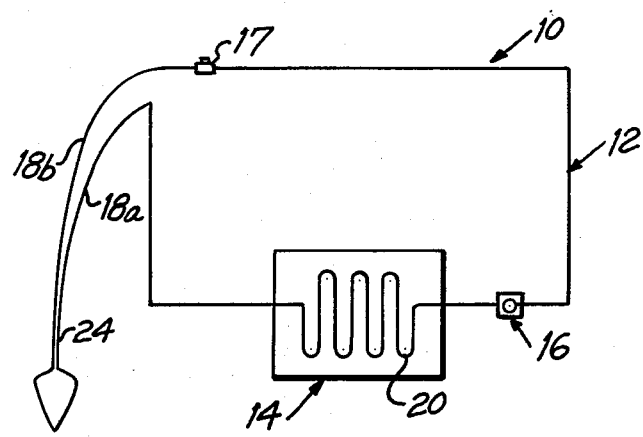
FIG. 1 is a schematic illustration of the hypothermia apparatus of the present invention.

Referring now to the drawings where like reference characters designate identical or corresponding parts throughout the several views, and more particularly to the schematic illustration of FIG. 1, the apparatus of the present invention, generally denoted as 10, includes a coolant circuit 12, apparatus 14 for refrigerating the coolant fluid, pump means 16 for circulating the coolant fluid through the circuit and a coolant fluid introduction element, which in the preferred embodiment comprises a three-way petcock 17.

Figure 2:
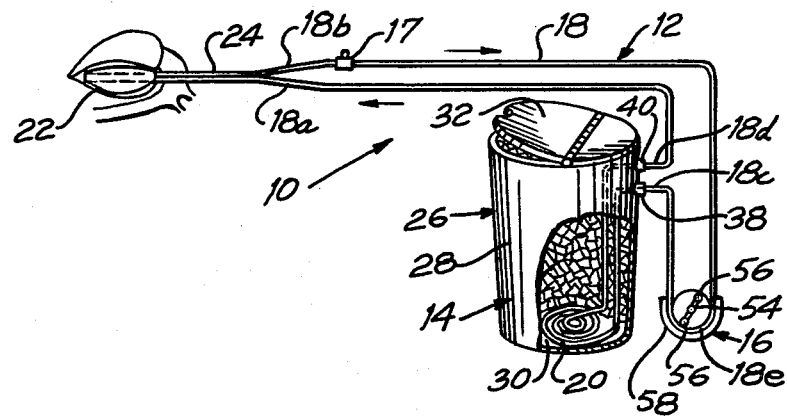
FIG. 2 is a perspective view schematically illustrating the hypothermia apparatus of the present invention.
Figure 8:
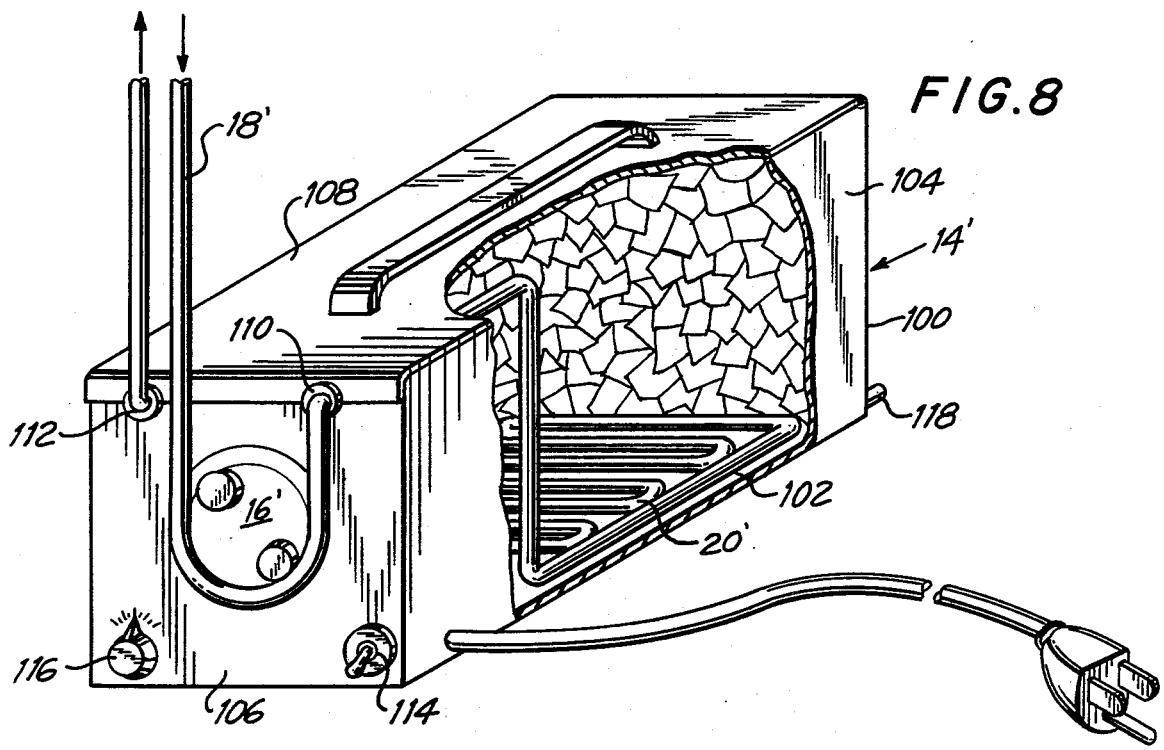
FIG. 8 is a schematic illustration of another embodiment of the cooling chamber of the present invention.

In the preferred embodiment of the invention, the coolant circuit 12 is of a disposable nature which may be discarded after use. Referring to FIG. 2, coolant circuit 12 comprises a length of flexible tubing 18 formed of any biocompatible material, such, forexample, as polyvinyl plastic or silicone. The tubing is integrally formed with a heat exchange portion 20 and a highly flexible, inflatable bag or balloon 22, which is fluidly connected to end portions 18a and 18b of flexible tubing 18 by a double lumen 24 having a pair of parallel passages formed therethrough, each passage merging into one of tube end portions 18a or 18b to provide a continuous fluid circuit. The heat exchange portion 20 preferably comprises an integral portion of the length of flexible tubing 18 which, although not necessary, may be formed of flexible tubing having a reduced wall thickness to facilitate thermal transfer. Further, the heat exchange section may have a configuration other than the particular one shown in FIG. 2. For example, the heat exchange portion may have a preformed flat serpentine path as illustrated in FIG. 8 or thin walled bag or tubular coil. However, it is desireable that the heat exchange portion 20 be integrally joined to the flexible tubing 18 without resort to any connectors, such as quick-connect couplers, which might provide a source of contamination for the coolant fluid circulating within the coolant circuit. Similarly, the connections between the double lumen 24 and the flexible, inflatable bag 22 on one end and the end portions of flexible tubing 18a and 18b on the other end are both integral connections as opposed to ones effected by couplings.

Referring to FIG. 4, the interior of double lumen 24 is divided into a pair of parallel passages 42, 44 by a wall, 46, and terminates in a portion which extends into the interior of bag 22. Fluid exit ports 48 are formed in the end portion of passage 42 within bag 22 while fluid entry ports 50 are provided in passage 44 within bag 22 in a position sufficiently spaced from that of exit ports 48 to provide good circulation of coolant but still within bag 22. The bag 22 is integrally sealed to lumen 24 at seam 52. The terminal end of flexible tube end portion 18a is integrally sealed to lumen 24 so as to fluidly communicate only with passage 42 while the terminal end of the other end portion 18b of flexible tube 18 is integrally sealed to lumen 24 so as to fluidly communicate only with passage 44.

Referring now to FIG. 1 in conjunction with FIG. 2, it is seen that the heat exchange portion 20 is located within the cooling apparatus 14. More particularly, referring to FIG. 2, the cooling apparatus 14 preferably comprises a cup-shaped container 26 having a substantially cylindrical side wall, 28, bottom wall, 30, and a hinged top wall 32 which provides access to the interior of the container 26. The interior surfaces of container 26 are preferably thermally insulated.

Container 26 is preferably formed of a suitable rigid plastic and it is intended that container 26, like the flexible tubing 18, double lumen 24 and inflatable bag or balloon 22 comprising coolant circuit 12, be of a disposable nature.

As seen in FIG. 2, the heat exchange portion 20 of coolant circuit 12 is positioned within container 26 and rests upon the bottom wall 30 thereof.

A pair of standard fittings 38, 40 are sealed, such as by cementing or gluing, within suitable openings formed in sidewall 28, of container, 26. The terminal ends of heat exchange portion 20 of tubing 18 are inserted and sealed from the interior of container 26 within respective fittings 38, 40. Similarly, terminal ends 18c, 18d of tubing 18 are sealed from the exterior side of container 26 within fittings 38, 40 respectively, thereby rendering heat exchange portion 20 integral with the remainder of the coolant fluid circuit 12.

In the preferred embodiment, container 26 is filled with a mixture of water and ice which directly contacts the heat exchange portion 20 of the coolant circuit, thereby cooling the coolant fluid contained therein. Although the refrigeration source within container 14 is illustrated in the preferred embodiment as ice, other refrigeration sources may be used. For example, a minaturized electrochemical system of an expanding and compressing refrigerant gas as commonly used in commercial refrigerators may be used or the heat exchange portion 20 may be wrapped around a receptacle adapted to receive a frozen bottle of saline or other suitable solution.

As mentioned hereinabove, it is an object of the present invention to reduce the possibility of contamination of the fluid circulating within the coolant curcuit. It is therefore necessary to provide means for circulating the coolant fluid through the coolant by means external thereto so that the sterility of the coolant fluid is not compromised. Referring to FIG. 2, a conventional roller-type pump, such for example, as a Manostat pump, generally denoted 16, is provided at a point upstream of heat exchange portion 20. Pump 16 includes a rotor 54 connected to an electrical motor on which are mounted a pair of diametrically opposed rollers 56. An annular race 58 circumscribes the rotor 54 and provides a seat for a portion 18e of flexible tubing 18 which is looped therearound so that upon rotation of rotor 54, the rollers 56 alternately bear against and depress a length of the wall of flexible tube portion 18c. The sequential, continual depression of the wall of tube portion 18c causes the coolant contained within flexible tube 18 to circulate through coolant circuit 12. The speed of rotation of rotor 54 (and consequently the rate of circulation and amount of cooling afforded thereby) may be varied by appropriately setting a speed control rheostat.

It has been found that the circulation of the coolant fluid at a rate of approximately 1 liter per minute is satisfactory. It is noted that pump 16 is not a part of the coolant circuit, so that the coolant fluid never "sees" the interior of the pump, but rather pump 16 operates completely externally to the coolant circuit 12. Thus, there is no danger of either compromising the sterility of the coolant fluid by virtue of the fluid coming into contact with a contaminated pump element or having a defective pump seal provide a passage through which air might enter the coolant curcuit. It also should be noted that coolant circuit 12 and container 26 may easily be disassociated from the pump 16 so that the pump may be retained for subsequent use.

The coolant which circulates through the coolant circuit 12 may be any conventional coolant fluid which is both sterile and biocompatible with human tissue. For example, such coolant fluids as sterile saline solution, or Ringer's solution may be used.

As mentioned hereinabove, prior systems which utilize flexible bags for applying topical hypothermia to organs and areas of the human body all are subject to the drawback that no adequate method is available for introducing the coolant fluid into the circuit in a manner such that the bag will be distended subsequent to its insertion in place so as to contact the optimum surface area of the organ to be treated. It is one object of the present invention to provide an apparatus and method for achieving this desirable result as described hereinbelow. Referring to FIGS. 3a–d, a three-way valve, such for example, as a conventional three-way petcock, 90 is inserted in line with flexible tubing 18, preferably at a point 18f,g, close to its downstream juncture with double lumen 24, i.e., proximate to or within tubing end portion 18b. The three-way petcock 90 is essentially a device having three interconnected passages 92a, b, c any two of which may selectively be coupled in fluid communication with each other with the third passage being sealed by conventional valve apparatus. The apparatus is preferably supplied to the hospital as shown in FIG. 3a with passage 92c of petcock 90 being connected to the upstream end 18f of tubing 18. To maintain the sterility of the coolant circuit during this time, a standard surgically accepted fitting, such as absorbant cotton and a nipple, are inserted in the open end of 18g of tubing 18. Alternatively, the apparatus may be delivered with petcock end 92a inserted into tubing end 18g. This junction can then be disconnected without compromising sterility.

Introduction of the coolant fluid is accomplished as follows. With petcock 90 adjusted to provide fluid communication between tubing end 18f and fluid passage 92b, a source of coolant fluid, such as a half-liter bottle, 94, of standard saline solution, is mounted on an I.V. pole in a raised position relative to coolant circuit 12 and the coolant fluid is directed under the hydrostatic head present due to the relative positions of bottle 94 and circuit 12 via an infusion line 96 and passage 92b into the coolant circuit. During this time, the bag 22 is prevented from expanding either by being held in the surgeon's or his assistant's hand or by being maintained in an appropriate disposable sleeve 93. When the coolant circuit (with the exception of the bag 22) has been completely filled as evidenced by overflow from the open end 18g of the tubing 18, the petcock 90 is turned off and the tubing end 18g is reconnected to passage 12a of the petcock 90. Infusion line 96 is then removed from petcock passage 92b. It is understood that the above procedure is a standard operating room maneuver commonly practiced in connection with other apparatus.

The bag 22 in its deflated configuration is then located within the bodily cavity or proximate to the organ to be treated. By experience and observation, the surgeon can guage the volume of the bodily cavity or organ. For example, if it was desired to fill the coolant bag 22 to contact the walls of a heart ventricle having a volume of about 30 cc., it would be understood that an additional 30 cc of coolant would be necessary to be added to coolant circuit 12 to accomplish optimal distension of bag 22. Thus, after inserting the bag 22 in its deflated condition into the ventrical, a syringe 98 (FIG. 3b) would be filled with 30cc of sterile saline solution and appropriately coupled to passage 92b of petcock 90. The petcock is opened as shown in FIG. 3b and the contents of syringe 98 injected into the coolant circuit. Since the coolant circuit 12 (with the exception of bag 22) is already filled with coolant fluid, the additional 30cc would then distend the extremely flexible bag by that amount, thereby filling the cavity. The petcock would then be closed as shown in FIG. 3c, i.e., the valve adjusted to provide fluid communication between passages 92a, c, the syringe removed, and the pump turned on, thereby initiating hypothermic or hemostatic cooling to the organ.

More particularly, referring to FIGS. 1, 2 and 3c, the coolant fluid which circulates through coolant circuit 12 under the action of pump 16, travels toward bag 22 from heat exchange section 20, through flexible tube end portion 18a, enters lumen passage 42 (FIG. 4) and is directed into bag 22 through exit ports 48. The coolant fluid circulates through bag 22 whereupon it enters lumen passage 44 through entry ports 50 and exits therefrom into flexible tube section 18b. With the bag filled with the coolant fluid, its outer wall surface is in contact with the wall surface of the cavity within which it is located (shown as the left ventricle of the heart in FIG. 4) to cool the same.

At the end of the procedure the surgeon would connect a suction line to passage 92b (FIG. 3d) of petcock 90 with the valve providing communication between passages 92b and 92c, to completely empty the coolant circuit 12 of coolant fluid thereby deflating the bag which is then easily removed from the cavity. The coolant circuit 12 and container 26 can then be discarded.

Thus, it can be seen that the apparatus of the present invention provides means by which the flexible bag 22 can be filled with an amount of coolant fluid specifically correlated to the volume of the bodily cavity within which it is to be used to effect optimal cooling thereof by assuring that the walls of the bag are in maximal contact with the walls of the organ.

It may be desirable to deliver the apparatus with the coolant circuit 12 comprising a closed loop rather than parted at tube ends 18f, g. In this case, the tubing 18 may incorporate a suitable multiple channel petcock to allow filling by providing adequate venting for the cooling fluid, bag distension, coolant flow and vacuum emptying.

Thus, apparatus for hypothermically treating a portion of the human body has been described wherein the coolant circuit and cooling chamber are disposable and easily disassociated from the pump which is retained for futher use. Means are provided for optimally filling the flexible bag to obtain maximal heat exchange with the organ being treated.

Referring to FIG. 4, the apparatus of the present invention is shown as being used to apply topical hypothermia to the left ventricle of the heart. As described hereinabove, prior to the present invention, the only methods of hypothermically treating the heart during open heart surgery wherein the aorta is occluded which permits surgery to be performed in regions surrounding the coronary arteries and aortic root has been by filling the open pericardium with a frozen saline slush or cooled Lactated Ringer's solution via a drip bottle and wall suction. Such methods can only cool the myocardium or outside of the heart even though it has been shown that subendocardial hypothermia is most important to prevent cellular damage from anoxia. It is another object of the present invention to form the flexible, inflatable bag 22 so that it is small enough to fit into the desired heart chamber, for example, the left ventrical. Thus, the flexible, inflatable bag may be introduced into the left ventrical, for example, via the left atrium 60 by way of the right superior pulmonary vein 62. Upon the coolant being circulated through the bag as described above, the subendocardium is cooled.

In this connection, the double lumen 24 or end portions 18a, b, of flexible tubing 18 may be marked with appropriate indicia (not shown) to identify the direction in which the luman and bag are to be inserted. For example, one side of the lumen may be marked to indicate that it is to be inserted facing upwardly to avoid being obstructed by the papillary muscles in the left ventricle.

Of course, the bag may be inserted within the appropriate heart chamber via other passages, such, for example, as a puncture wound.

Referring to FIG. 5, a modification of the above invention is shown wherein a flexible, inflatable bag 64 is formed in the shape of a thin bladder having a large surface area. The bag 64 is positioned to lie between, for example, the heart 66 and the opened pericardium 68 in order to provide cooling to the myocardium or outer surface of the heart. Rather than using a double lumen, as described above, separate fluid flow passages 70, 72 may be utilized. Coolant fluid exits from the flexible tubing 18 into fluid passage 70 and into bag 64 where it circulates and cools the myocardium. The coolant then leaves bag 64 and enters flexible tubing 18 through passage 72. Fastening means 74 may be provided to close the bag around the heart to provide hypothermia to a larger surface area of the organ should conditions so warrant. Fastening means may be of any suitable type, such as button flap, Velcro tape or other suitable means. The bag 64 may be provided with internal channels to insure complete coolant fluid circulation when the bag is folded over the heart and in order to avoid any warm spots in the bag.

Referring to FIG. 5a, the bag 64 may also include a heat insulating layer 65 affixed to its lower surface, i.e., at the interface between the pericardium and the cooling bag. Layer 65 preferably comprises a flexible blanket formed of a suitable biocompatible material, such for example, as a closed cell urethane foam. Layer 65 maintains the subendocardial cooling effect and allows the entire heart (or other organ) to be cooled by conduction since the heart is insulated from the ambient environment. Additionally, insulating layer 65 may be used in conjunction with bag 64 as described or as a separate element. When so used in conjunction with an interventricular cooling bag, since during the latter stages of an open heart surgical procedure, the chilled blood in the supporting heart-lung-patient circuitry is rewarmed preparatory to defibrillating the patient's heart, the insulating layer 65 will maintain the low temperature of the heart by insulating it from the warming body, thereby extending myocardial protection for several more minutes.

It is understood that although the above description of the use of the bladder type of inflatable bag has been in conjunction with hypothermia of the heart, other organs may be so treated in a similar manner. Further, both the bladder embodiment and the smaller bag embodiment may be used separately or together to ensure optimal protection from cellular damage due to anoxia.

Turning now to FIG. 6, a modification of the present invention is shown wherein a catheter 76 is incorporated into the double lumen 24 so that the catheter lies parallel to the passages therein. Catheter 76 extends completely through bag 22 so that there is no communication between its bore and the interior of bag 22. The terminal end 77 of catheter 76 communicates with the interior of the cavity in which bag 22 is located, illustratively shown in FIG. 6 as being the left ventricle of the heart. The other terminal end 79 of catheter 76 opens into the atmosphere. Catheter 76 functions as a passage for venting air from the heart chamber prior to restoring cardiac circulation.

It is well known that cooling has a restrictive effect on the blood vessels, narrowing their bores and thereby reducing the flow of blood within these vessels, thereby controlling bleeding or hemorrhaging. It is also well known that mechanical pressure applied to a torn blood vessel will also encourage hemostasis.

In this connection, the flexible bag may be inserted into a cavity whose wall is hemorrhaging, the bag being filled with coolant and cooling applied to the cavity wall in the same manner as described hereinabove in connection with the application of topical hypothermia. For example, referring to FIG. 7, an appropriately shaped bag 78 in a deflated condition is introduced through cervix 82 into a hemorrhaging uterus 80 and then filled as described above. Since the double lumen 24 may be very small in diameter (only being large enough to maintain coolant circulation at the desired rate under the action of roller pump 16), insertion via the cervix 82 can be easily accomplished. It is now possible for the surgeon to observe whether hemorrhaging was abated by merely withdrawing all or some of the coolant fluid from the bag 78 momentarily by the use of a sterile syringe being connected to the petcock. If the bleeding recommences the surgeon need only reinject the aspirated amount of coolant fluid within the syringe.

It should be understood that the present invention has hemostatic applications other than in the uterus. For example, the inflatable bag may be formed in a smaller version and may be inserted into a nostril to control nasal bleeding by hypothermia and incidental pressure.

Referring to FIG. 8, another embodiment of the cooling chamber, designated 14', is shown. Whereas a disposable cooling chamber such as is shown in FIG. 2, is normally preferred, cooling chamber 14' is designed to be retained after use. Cooling chamber 14' comprises a generally box-shaped container 100 defined by a bottom wall 102, a pair of opposed side walls 104, a front wall 106, and a rear wall (not shown). An upper cover 108 is hinged to the top of the rear wall to provide access to the interior of container 100. The heat exchange portion 20' of flexible tubing 18' is located within container 100 against bottom wall 102. Flexible tubing 18' enters into container 100 through an entry port 110 and exits therefrom through an exit port 112. Ports 110, 112 are defined at the intersection between cover 108 and front wall 106 and are suitably gasketed to maintain the interior of the container sealed. A conventional roller-type pump, 16', is affixed to front wall 106 having the same general construction as pump 16 described hereinabove. Switch 114 and rheostat dial 116 control the supply of power to and speed of pump 16'. As before, the interior of container 100 is filled with an ice-water mixture to cool the coolant fluid circulating through the coolant fluid circuit. A drain port 118 may be provided.

Obviously, numerous modifications and variations of the present invention are possible in the light of the above teachings. For example, the pump may be of any suitable tube pump type in lieu of the roller-type pump described hereinabove. Additional configurations of the flexible, inflatable bag are possible, depending upon the desired use thereof, while the particular refrigeration means used to cool the coolant fluid may be as desired. It is therefore to be understood that within the scope of the appended claims, the invention may be practiced otherwise than as specifically described herein.

We claim:

1. A method of cooling a region of the human body comprising the steps of:
    providing a coolant circuit assembly including a length of flexible tubing and a flexible, inflatable bag fluidly coupled to said tubing by a lumen having at least two parallel passages formed therethrough;
    while maintaining the bag in a deflated condition, introducing coolant fluid into the entire coolant circuit except for the bag;
    introducing said deflated flexible bag into the region to be treated;
    introducing additional coolant fluid into the coolant circuit thereby inflating the bag, the additional coolant fluid being introduced in an amount based upon the volume of the region of the body to be coated;
    cooling said coolant liquid; and
    circulating said coolant fluid through said coolant circuit.

2. A method as recited in claim 1 for cardiac hypothermia wherein said introducing step comprises introducing said flexible bag into a ventricle of the heart through a pulmonary vein.

3. A method as recited in claim 1 further including the step of prior to circulating said coolant fluid, positioning a substantially thin bladder between the organ containing the region to be treated and the contiguous region of the body.

4. A method as recited in claim 1 further including the step of prior to circulating said coolant fluid, positioning an insulating layer member between the organ containing the region to be treated and the contiguous region of the body.

5. A method of using apparatus for cooling an organ or body cavity, which apparatus includes;
    a coolant circuit assembly including a length of flexible tubing, said length of flexible tubing including a heat exchange portion and a flexible, inflatable bag fluidly coupled to said flexible tubing by a lumen having at least two parallel passages formed therethrough, said coolant circuit being adapted to contain a sterile coolant fluid;
    means for circulating the coolant fluid through the coolant circuit, said circulating means being entirely external to the path of said coolant fluid through said coolant circuit;
    means in thermal exchange relationship with said heat exchange section of said length of flexible tubing for cooling said coolant fluid; and
    valve means provided within the coolant circuit assembly, including a first fluid conduit portion forming a part of the coolant circuit assembly and a second fluid conduit portion fluidly communicating between said first conduit portion and the external environment including an inlet extending into said external environment adapted to receive a supply of coolant fluid from a reservoir thereof, and gating means for sealing said first conduit portion from said second conduit portion, said valve means being for selectively alternately providing external fluid communication to the interior of said coolant circuit and for fluidly sealing said coolant circuit; said method comprising the steps of:
    adjusting said gating means to provide fluid communication between said first and second fluid conduit portions;
    maintaining said inflatable bag in a deflated condition;
    connecting a reservoir of coolant fluid to said inlet of said second fluid conduit portion thereby introducing coolant fluid into the entire coolant circuit assembly except for the bag;

locating the bag in a deflated condition into a region of the body to be cooled while removing all constraints from the bag so that it can be inflated;

introducing additional coolant fluid into the coolant circuit assembly through said second fluid conduit portion thereby inflating said bag, said additional coolant fluid being introduced in an amount corresponding to the volume of the region to be cooled;

adjusting said gating means to seal said first conduit portion from said second conduit portion; and circulating said coolant fluid through said coolant circuit.

* * * * *